United States Patent [19]

Topol et al.

[11] 4,451,152

[45] May 29, 1984

[54] METHOD FOR MEASURING THE RADIATION TRANSMITTING PROPERTIES OF A FLUID

[75] Inventors: George J. Topol, Gaithersburg; Chadwick L. Trent, College Park, both of Md.

[73] Assignee: Monitek, Inc., Hayward, Calif.

[21] Appl. No.: 457,141

[22] Filed: Mar. 7, 1983

Related U.S. Application Data

[63] Continuation of Ser. No. 254,891, Apr. 16, 1981, abandoned, which is a continuation of Ser. No. 709,923, Aug. 18, 1976, abandoned.

[51] Int. Cl.³ .................... G01N 21/03; G01N 21/15
[52] U.S. Cl. .................................... 356/440; 356/246
[58] Field of Search .................. 356/436–442, 356/409, 411–415, 246; 250/573–577

[56] References Cited

U.S. PATENT DOCUMENTS

| 2,315,944 | 4/1943 | Dick | 92/245 |
| 3,572,952 | 3/1971 | Anthon | 250/576 |
| 4,245,914 | 1/1981 | Clack | 356/246 |

FOREIGN PATENT DOCUMENTS

| 1228933 | 9/1960 | France | 128/218 P |
| 55-51339 | 4/1980 | Japan | 356/442 |

Primary Examiner—Bruce Y. Arnold
Attorney, Agent, or Firm—Harvey G. Lowhurst

[57] ABSTRACT

There is disclosed a method for sampling and examining a fluid from a tank or flow line to determine density or turbidity, including a sampling chamber attached to the tank or line with a piston in a chamber. The piston is provided with a sealing ring which circumscribes one end of the piston and which provides a fluid-tight seal within the chamber so that moving the piston away from the tank or line pulls a sample into the chamber. The sealing ring comprises a main body portion which circumscribes the piston and is in contact therewith but which is not in sealing engagement with the chamber. Extending outwardly from the main body portion of the sealing ring and integral therewith is a frusto-conical skirt. The outermost edge of the frusto-conical skirt is in sealing contact with the cylinder. A light source is provided to transmit light into the sample and a photodetector is provided to detect light from the interior of the chamber. The photodetector generates an electrical signal proportional to the light transmissivity of the fluid and the signal is analyzed to determine turbidity. The chamber can be provided with transparent walls, or can be totally transparent, to simplify light transmission. The piston, after the measuring process, returns the sample to the tank or line and simultaneously wipes the interior of the chamber clean.

1 Claim, 5 Drawing Figures

METHOD FOR MEASURING THE RADIATION TRANSMITTING PROPERTIES OF A FLUID

This application is a continuation of application Ser. No. 254,891, filed Apr. 16, 1981, now abandoned, which in turn, was a continuation of application Ser. No. 709,923, filed Aug. 18, 1976, now abandoned.

This invention relates to an improvement in a device for measuring turbidity, suspended solids and sludge levels.

A device which has been used in the past to measure turbidity, suspended solids and sludge levels in a sewage treatment plant, which is sold under the trademark CLAM, comprises a chamber which is placed in communication with the sludge settling portion of a settling tank in a sewage treatment plant, the chamber containing a piston. The piston is in fluid-tight relationship with the interior walls of the chamber so that movement of the piston away from the sewage causes a sample to be drawn into the chamber. Optical means are provided at the chamber to transmit light through transparent wall portions thereof and through the sample to produce a signal representative of received light level and hence, representative of the fluid density. To insure that the piston is in fluid-tight relationship with the chamber, the piston is provided with a sealing ring. It has now been found that the design of this sealing ring is very critical to long lasting, trouble free operation of this device.

In accordance with the practice of this invention, there is provided an apparatus for measuring the radiation transmitting properties of a fluid sample from a relatively large volume of the fluid. The apparatus comprises, in combination, a sample chamber having a volume significantly less than the larger volume which it is sampling, and means for connecting the sample chamber into direct communication with the larger volume. The sample chamber contains a piston which is movable within the chamber between a first position and a second position, the movement permitting a simple of fluid to be drawn from the larger volume into the chamber. The piston is provided with a sealing ring which circumscribes one end of the piston and which provides a fluid-tight seal within the chamber. The sealing ring comprises a main body portion which circumscribes the piston and is in contact therewith but which is not in sealing engagement with the chamber. Extending outwardly from the main body portion of the sealing ring and integral therewith is a frusto-conical skirt. The outermost edge of the frusto-conical skirt is in sealing contact with the cylinder. A source of electromagnetic radiation is disposed at the sample chamber for illuminating the sample drawn into the chamber. A detector means responsive to electromagnetic radiation is disposed at the sample chamber for receiving radiation passing through a sample drawn into the chamber and for producing an electrical signal representative of the level of received radiation. The apparatus further includes a means responsive to the electrical signal for indicating the magnitude of the signal as a measure of the radiation transmitting properties of the sample.

The invention will be more fully described by reference to the drawings wherein.

Figure 1:
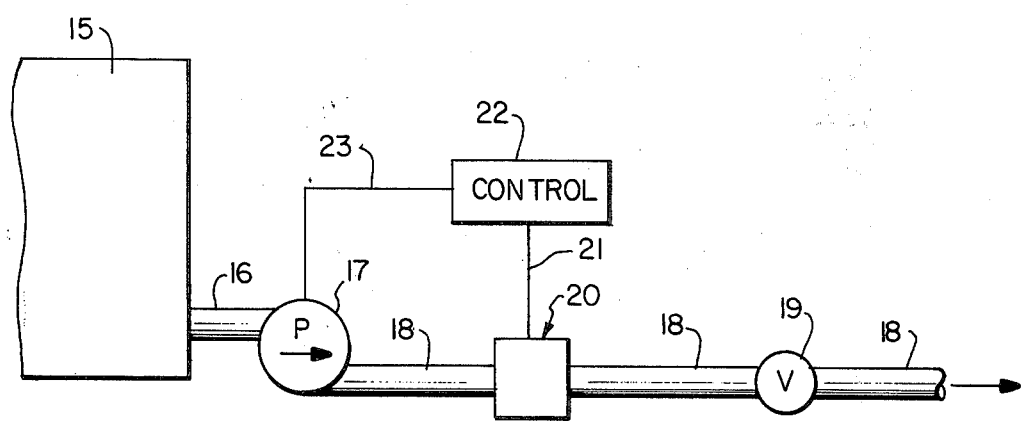
FIG. 1 is a schematic diagram illustrating this invention.

Referring now to the drawings in detail, it will be seen that FIG. 1 shows a system for extracting materials from the bottom of a tank, e.g., a secondary settling tank in an activated sludge sewage treatment system, indicated generally at 15. A conduit 16, which would normally be of relatively large diameter adequate to carry large pieces of material as well as smaller particles, is connected near the bottom of the tank and to a pump 17. Pump 17 is of any suitable conventional type designed to pump materials having irregular and variable density and viscosity and delivers the fluid to a further conduit 18. Conduit 18 includes a valve 19 which is incorporated to prevent reverse flow of the fluid and to permit conducting the fluid to a digestor or other further processing equipment.

Disposed along conduit 18 between the pump and the valve is a sampling and sensing apparatus 20 capable of determining the light transmission properties of the fluid passing through conduit 18 and of producing the electrical signal representative of density or turbidity of the fluid, which electrical signal is delivered by conductor 21 to a control unit 22. Either device 20 or control unit 22 can include means for referring the detected light level to a preselected threshold so that when the fluid passing through the conduit becomes clear enough to satisfy preselected conditions, the control unit acts, through an electrical signal on line 23, to deactivate the pump and terminate the process of extracting materials from the bottom of tank 15.

The above system is primarily intended for extracting sludge from the bottom of a settling tank so that the pump can be activated to withdraw sludge and the sludge being withdrawn can be tested to be sure that only sludge, and not clear water, is being withdrawn. If desired, timing means can be incorporated in control unit 22 to periodically energize the pump, extract some material from tank 15 and deliver it to measuring device 20 which can sample the substance and determine whether the pump should stop or continue running. If not, the pump can be promptly deenergized, thereby eliminating unnecessary withdrawal of material from the tank. By limiting withdrawal from the tank to only those substances which can be regarded as treatable sludge, the pump time can be minimized and the digestor or other processing equipment to which conduit 18 delivers material from the tank will not be unnecessarily overloaded with low density materials which it cannot efficiently handle.

Figure 2:
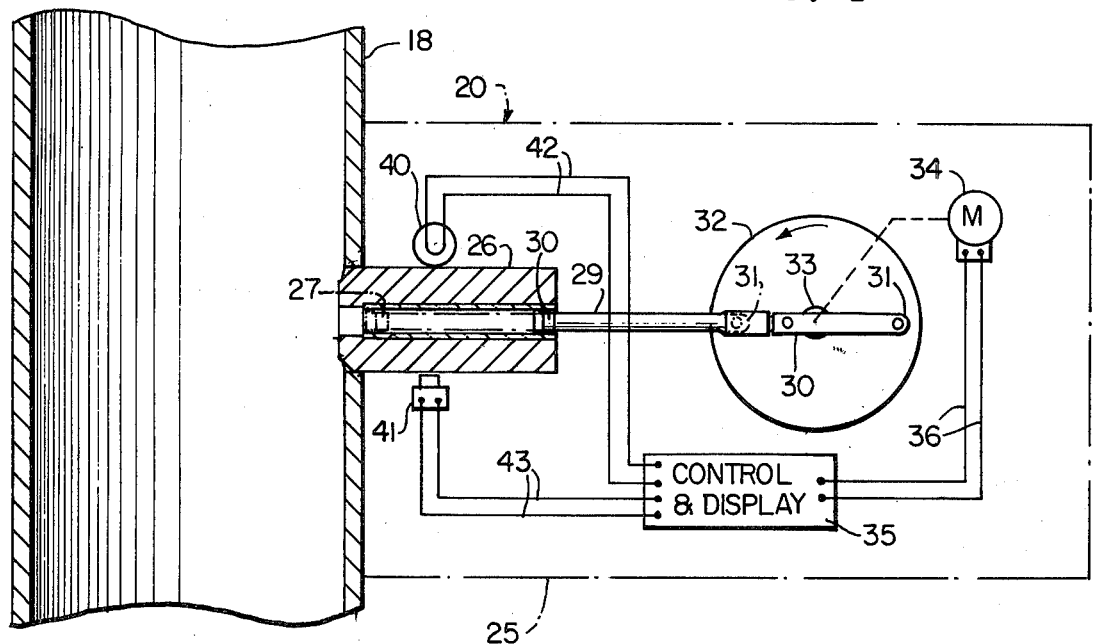
FIG. 2 is a diagram schematically illustrating a sampling and testing apparatus used this invention.

The apparatus for sampling and measuring the density of the fluid passing through conduit 18 is shown in FIG. 2. As shown therein, the sampling apparatus indicated generally at 20 is enclosed within a light-tight container indicated schematically by dotted lines 25 to exclude ambient light from the measuring apparatus. Not all of the apparatus shown within the dotted lines need be maintained in a dark environment, but can be if desired.

Specifically, the apparatus includes a cylindrical chamber 26 which is firmly connected, in water-tight relationship, to an opening in a wall of conduit 18. As shown in FIG. 2, chamber 26 has totally transparent walls. However, this is not a necessary requirement as the chamber can be manufactured from any convenient material, opaque or otherwise, with suitably disposed transparent wall portions.

Contained within chamber 26 is a piston 29 which is moveable in the direction of the axis of the cylindrical chamber from a position adjacent the opening into conduit 18 to a position near the outer end of chamber 26. The surfaces of piston 29 adjacent the walls of the chamber are provided with sealing means, described more fully hereinafter, to provide a water-tight seal between the piston and the interior of chamber 26. One end of a connecting rod 30 is pivotally attached to the apparatus, the connecting rod 30 being journalled to a pin 31 which is eccentrically mounted on a wheel 32, the wheel being rotatable about an axle 33. Axle 33 is mechanically coupled to a drive motor 34 which can be energized to rotate the wheel continuously or sporadically, as desired.

Motor 34 is energized by, and is under the control of, signals from a control and display unit 35 which provides the necessary control signal via conductors 36. It will be recognized that continuous rotation of motor 34 will cause continuous rotation of the crank wheel 32 which, through the eccentric pin and connecting rod, will cause piston 29 to move from the position shown in FIG. 2 to the position shown in dotted lines adjacent opening 28 during 180° rotation of wheel 32. Then, during the subsequent 180° of rotation, the piston is withdrawn again to its original position.

As previously mentioned, the piston is provided with means to provide a fluid-tight seal with chamber 26. This is more clearly shown in FIG. 3 wherein piston 29 is shown to be provided with a sealing ring 27. The sealing ring 27 is shown in enlarged detail in FIG. 4 and its interengagement with the piston rod 29 and the chamber 26 is illustrated in more detail in FIG. 5.

Figure 4:
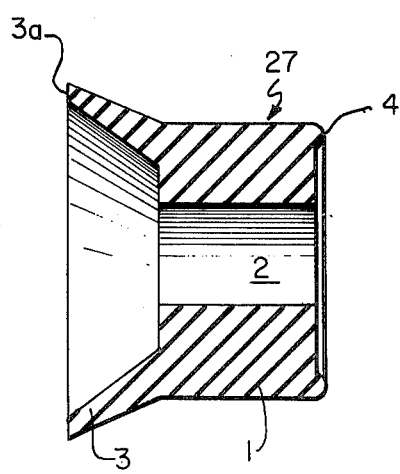
FIG. 4 is a cross section of a sealing ring used with this invention.

Referring more specifically to FIG. 4, the sealing ring 27 comprises a main body portion 1 through which extends a longitudinal bore 2. A frusto-conical skirt 3 extends outwardly from the main body portion 1 and terminates in a flat forward end 3a. A slight protuberance 4 projects from the other end of the main body portion 1.

Figure 5:
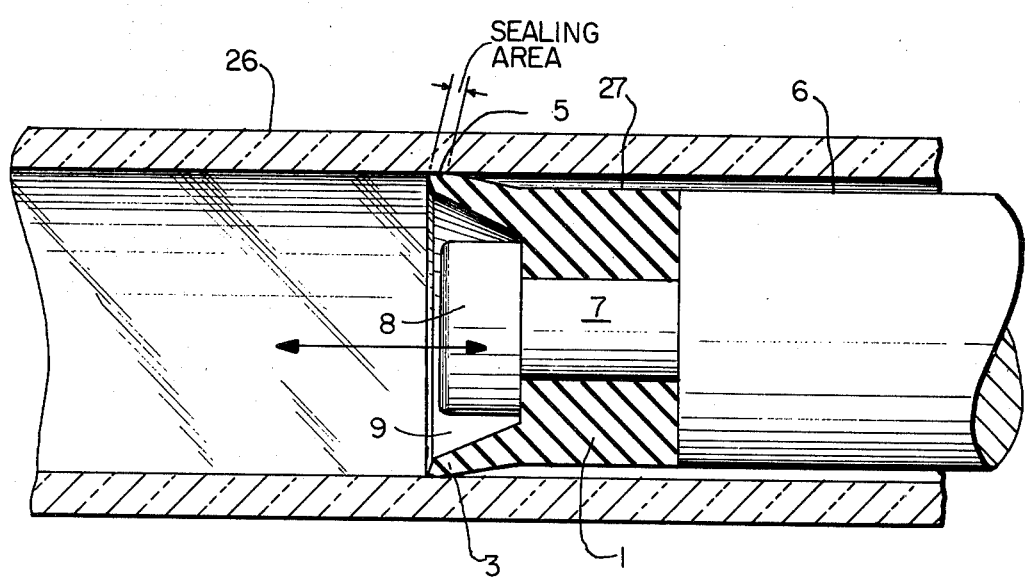
FIG. 5 is a cross sectional view of a portion of the apparatus used with this invention.

As shown in FIG. 5, the distance between the outer edges of the skirt 3 is slightly greater than the inner diameter of the chamber 26. Thus, the end of the skirt 3 is partially deformed when it is within the chamber 26 resulting in a sealing area 5. This is the only point of contact between the sealing ring 27 and the glass chamber 26.

It will be appreciated that the sealing area 5 is a flat edge rather than being a feather edge since a feather edge would tend to wrinkle in use and/or crack, both of which would lead to leakage.

Figure 3:
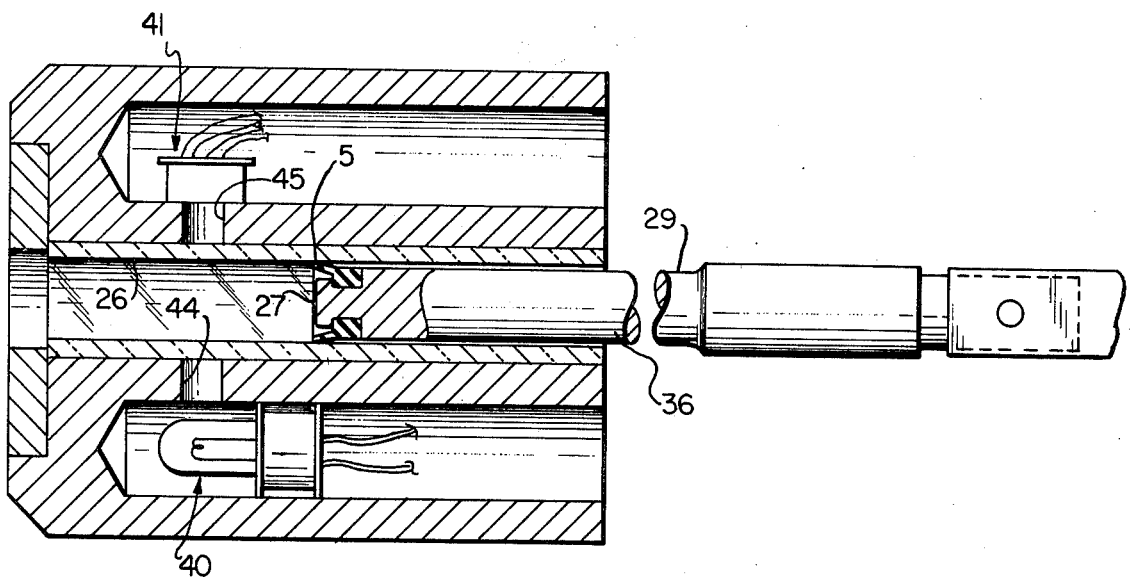
FIG. 3 is a detail in partial section of a sampling and testing apparatus used with this invention.

As shown in FIGS. 3 and 5, the piston 29 contains a main body portion 6, a smaller neck portion 7 having a diameter considerably less than that of the main body portion 6, and a head portion 8. The diameter of the head portion is larger than the diameter of the neck portion 7 but smaller than the diameter of the main body portion 6. To assemble the sealing ring 27 with the piston rod 29, the bottom of the bore 2 is placed over the head 8 and forced down until the bore 2 engages the neck portion 7. The diameter of the bore 2 is approximately equal to the diameter of the neck portion 7. The skirt 3 of the sealing ring 27 flares outwardly from the head 8 of the piston rod, forming a conical cavity 9 on the end of the piston rod.

The sealing ring 27 not only provides a fluid-tight seal within the chamber 26 but also performs the function of cleaning the interior of the cylinder. Thus, on each ejection stroke, during which the piston 29 moves from the open end of the cylinder to the end adjacent the opening, the piston pushes the sample of material previously tested back into the larger volume of the flow line and simultaneously wipes substantially all foreign matter from the interior walls of the chamber.

The sealing ring can be of any resilient material, such as rubber, plastic, or the like and is preferably polyurethane. The configuration of the seal and its interengagement with the piston and, more particularly, the inner walls of the chamber 26 is critical. It has been found that rings of other configurations, e.g., O-rings, rings having square cross sectional configurations, etc., are quite subject to abrasion due to abrasives which are present in sewage, such as the abrasives present in toothpaste, etc. and tend to develop leaks after a few hours of operation. By contrast, the sealing rings used in the practice of this invention, because of their unique configuration, are highly resistant to abrasion and will last several years under normal operating conditions.

Referring to FIGS. 2 and 3, the means for determining the light-transmission characteristics of the sample drawn into the chamber includes a light source 40 and a photodetector 41. The light source is energized through conductors 42 from the control and display unit, and the photodetector provides to the control and display unit electrical signals on conductors 43, these signals being representative of the light level received from source 40 through chamber 26. The light passes from the light source 40 through aligned bores 44 and 45 to the photodetector 41.

What is claimed is:
1. The method of sampling and examining the optical radiation transmitting properties of a fluid contained in a large volume of fluid comprising the steps of:
   communicating the large volume of fluid with a sample chamber which has at least a pair of aligned optically transparent wall portions forming windows through which the optical radiation can pass through the fluid;
   selecting a piston for the sample chamber, for drawing a fluid sample from the large volume of fluid into the sample chamber, which has an external diameter smaller than the internal diameter of the sample chamber to form a separation between the piston wall and the sample chamber wall sufficiently larger to insure lack of contact between the piston and the sample chamber to prevent scratching;
   passing optical radiation from a source through the fluid sample to a detector for determining the optical radiation transmitting properties; and
   fluid tightly sealing one end of the movable piston to the internal wall of the sample chamber with a seal which is shaped and dimensioned to also wipe the windows of the sample chamber without scratching by forming the seal with a main body portion which circumscribes the piston in sealing contact therewith but which is spaced apart from the sample chamber wall to avoid scratching that wall with debris in the fluid sample and with a structural frustoconical skirt integral with and extending outwardly from the main body portion and terminating the skirt in a flat forward end portion which is substantially at right angles to the center line of the piston and which has an external diameter at the outermost edge of the end portion slightly greater than the internal diameter of the sample chamber so that the outermost edge of the end portion seals against the sample chamber wall and the flat forward end portion is partially deformed by the sample chamber to inwardly and rearwardly taper the flat forward end portion to wipe the debris from the wall and to cause the debris to fall away from the wall inwardly when expelling the fluid sample from the sample chamber.

* * * * *